(12) United States Patent
Webber et al.

(10) Patent No.: US 6,329,561 B1
(45) Date of Patent: Dec. 11, 2001

(54) IMPURITIES REMOVAL

(75) Inventors: Kenneth M. Webber; Mark P. Kaminsky, both of Friendswood, TX (US); Andrew P. Kahn, Eagleville, PA (US)

(73) Assignee: Equistar Chemicals, LP, Houston, TX (US)

( * ) Notice: Subject to any disclaimer, the term of this patent is extended or adjusted under 35 U.S.C. 154(b) by 0 days.

(21) Appl. No.: 09/671,071

(22) Filed: Sep. 27, 2000

(51) Int. Cl.[7] .............................. C07C 7/163; C07C 5/02; C10G 45/00
(52) U.S. Cl. ..................... 585/809; 585/259; 585/261; 585/258; 585/510; 208/142; 208/143; 208/144; 208/263
(58) Field of Search ...................................... 585/809, 259, 585/261, 258, 510; 208/142, 143, 144, 263

(56) References Cited

U.S. PATENT DOCUMENTS

| 4,197,185 | * | 4/1980 | Le Page et al. ................. 208/71 |
| 5,811,608 | | 9/1998 | Stine et al. . |
| 5,847,252 | | 12/1998 | Stine et al. . |
| 5,877,372 | | 3/1999 | Evans et al. . |
| 5,895,830 | | 4/1999 | Stine et al. . |

* cited by examiner

*Primary Examiner*—Walter D. Griffin
*Assistant Examiner*—Tam M. Nguyen
(74) *Attorney, Agent, or Firm*—William C. Long

(57) ABSTRACT

The method of producing high purity isooctane useful as a gasoline blending component from diisobutylene or isooctane contaminated with minor amounts of oxygenated impurities which comprises converting the impurities at conditions of elevated temperature and pressure to hydrocarbon and water and recovering the purified diisobutylene or isooctane stream.

4 Claims, No Drawings

IMPURITIES REMOVAL

BACKGROUND OF THE INVENTION

1. Field of the Invention

The present invention relates to the removal of oxygenated impurities from hydrocarbons such as isooctane and diisobutylene. More particularly, the present invention provides a process for producing diisobutylene and/or isooctane, which is substantially free of oxygenated contaminants, which contaminants if not removed interfere with the successful use of the hydrocarbons as internal combustion engine fuels.

2. Prior Art

The present invention is especially adapted for the production of high purity isooctane and/or diisobutylene from $C_4$ hydrocarbon streams comprising substantial quantities of unsaturated butenes. A $C_4$ stream containing unsaturated hydrocarbons can be obtained by cracking an appropriate saturated hydrocarbon stream or alternatively by dehydration of tertiary butyl alcohol which is co-produced in the Oxirane process. Technology is known for the dimerization of isobutylene from either source in high selectivity to produce diisobutylene and the subsequent hydrogenation of the diisobutylene to form isooctane. Illustrative of references demonstrating this particular art is Evans U.S. Pat. No. 5,877,372.

A disadvantage of prior procedures is that the diisobutylene and isooctane thus obtained contain small but significant amounts of oxygenated impurities. For example, the hydrocarbons may contain oxygenated impurities ranging from about 0.1 wt % to as much as 5 wt % of the isooctane or diisobutylene. Normally such oxygenated impurities are ethers, alcohols, acids, ketones and the like materials. The presence of oxygenated impurities in the diisobutylene or isooctane is undesirable in that these contaminants substantially decrease the utility of the diisobutylene or isooctane in internal engine combustion fuels such as gasoline blends.

SUMMARY OF THE INVENTION

In accordance with one embodiment of the invention, diisobutylene is treated in order to convert oxygenated impurities contained therein to hydrocarbon and alcohol which are readily separated.

In accordance with another embodiment the present invention, a process is provided whereby diisobutylene is converted to isooctane and contained oxygenated impurities are converted to hydrocarbon and water in either a one-step or two-step procedure. In one practice of this embodiment, a one-step process, diisobutylene which is obtained by the dimerization of isobutylene and which contains oxygenated impurities, is hydrogenated in order to convert the diisobutylene to isooctane. As a feature of the hydrogenation, the conditions are adjusted so that during the hydrogenation conversion of the oxygenated impurities also takes place thus providing an end product of satisfactory purity. In another practice, a two-step process, isooctane is is obtained by the hydrogenation of diisobutylene at relatively mild conditions such that the oxygenated impurities are essentially unchanged and the isooctane thus formed is treated in a separate reaction step in order to convert the oxygenated impurities contained therein to hydrocarbon and water; hydrogen may or may not be employed.

DETAILED DESCRIPTION

Various methods are known in the prior art for the dimerization of isobutylene and for the production of isooctane. Reference can be made to U.S. Pat. No. 5,877,372 which illustrates a particularly favorable method for the production of isooctane wherein isobutylene is selectively oligomerized to mainly diisobutylene and the product diisobutylene is hydrogenated to isooctane. The disclosure of this patent is hereby incorporated herein in its entirety by reference. There are a great number of additional references which also illustrate the production of isooctane from a $C_4$ hydrocarbon stream by various procedures. Reference can be made to U.S. Patents such as U.S. Pat. Nos. 5,811,608, 5,847,252, 5,895,830, and the like. The disclosures of these references is hereby incorporated by reference it being understood that the dimerization of isobutylene and production of isooctane from $C_4$ hydrocarbon streams is by now a well known and well established art.

The diisobutylene produced by conventional procedures contains a small but contaminating amount of oxygenated materials, illustratively ethers, alcohols, ketones and like. An illustrative range of these impurities is 0.1 to 5 wt % based on diisobutylene. The presence of such impurities is sufficient to adversely effect the utility of the diisobutylene itself and, if carried through to product isooctane significantly lowers the value of the isooctane in a gasoline pool. It is extremely advantageous to provide a procedure whereby such oxygenated materials can conveniently be converted to non-deleterious materials. It should be noted, that due to the closeness in the boiling points of the oxygenated impurities and the various hydrocarbon materials, distillation is not a convenient method by which a separation can be accomplished.

In accordance with the present invention, in one particular embodiment, diisobutylene containing the oxygenated impurities is reacted at elevated temperature and pressure to convert the oxygenated impurities, eg. ethers, to hydrocarbon and alcohol which are readily separable. Diisobutylene substantially free of oxygenated impurities is readily obtained which has utility itself as a fuel component. In another embodiment, the impurities-containing diisobutylene is treated in one or two steps to produce isooctane free of the impurities. In the first embodiment of the invention described above, a diisobutylene stream containing the oxygenated impurities is subjected to a treatment whereby the oxygenated impurities are converted to hydrocarbon and alcohol or water. This treatment can be described as a high temperature ether cracking step whereby diisobutylene containing the oxygenates is heated to a temperature in the range of 50 to about 400° C. while in contact with suitable catalyst such as a nickel on silica catalyst. Although hydrogen can be used in this high temperature cracking, it is not necessary in order to accomplish the impurities conversion. The purified diisobutylene can be hydrogenated in conventional fashion to isooctane if desired.

Alternatively, in further embodiments of the invention, the diisobutylene containing oxygenated materials can be treated under conditions such that both hydrogenation of diisobutylene to isooctane takes place and also the ethers and other oxygenated materials contained therein are converted to hydrocarbon and water or alcohol. This hydrogenation can be carried out conveniently in either one or two steps. In a one step procedure the hydrogenation is carried out under conditions of sufficient severity to not only hydrogenate the diisobutylene but also to convert the oxygenated materials to hydrocarbon and water. Such a procedure is, however, less advantageous since side reactions tend to occur under the more severe conditions of hydrogenation. An alternative procedure is to stage the hydrogenation such that the great bulk is carried out under modest conditions whereby diisobutylene is selectively converted to isooctane and thereafter the conditions are made more severe for a relatively short period of time in order to accomplish the oxygenate conversions. These procedures will be illustrated in the following Examples.

EXAMPLE 1

Purification of Diisobutylene

A feed mixture simulating that resulting from isobutylene dimerization and comprised of 49.4 wt % diisobutylene, 1.3 wt % isobutylene trimer, 0.11 wt % sec-butyl-tert-butyl ether and 49.2 wt % isooctane was prepared, the ether being one of the main impurities normally associated with diisobutylene.

A commercial Ni/SiO2 catalyst sold by Englehardt and comprised of about 60 wt % Ni (10 cc 1/16"×3/16" extrudate) was charged to the fixed basket of a CSTR (135 cc). The feed mixture was contacted with the catalyst at reaction conditions of 150 cc/h feed flowrate, 32 SLH N2 flowrate and a reactor pressure of 400 psig. The following results were obtained:

| Temperature (° C.) | 200 | 250 |
|---|---|---|
| Ether conversion (%) | 48.2 | 73.7 |

No olefin conversion or alkane cracking products were observed, and a product diisobutylene substantially reduced in oxygenate content was obtained.

EXAMPLE 2

Two Step Diisobutylene to Isooctane Process

The commercial Ni/SiO$_2$ catalyst used in Example 1 (30 cc, 1/16"×3/16" extrudate) was charged to an upflow plug flow reactor (0.81" ID, 0.25" OD thermowell). A feed comprised by weight of 55.3% isooctane, 39.1% 2,4,4-trimethylpentene (DIB), 0.9% dimethylhexenes (DMH), 1.0% other trimethylpentenes (TMP), 2.9% trimers, 0.53% sec-butyl-tert-butyl-ether (SBTBE), 0.14% di-sec-butylether (DSBE) and 0.11% 2,4,4-trimethylpentane-2-ol (TMP-2OL) was fed over the catalyst at 150 cc/h, recycle ratio=1,400 psig reaction pressure, average bed temperature of 117° C. and a H2 feed rate of 66 SLH. Under these test conditions, the following conversions were obtained: DIB= 97.4%, DMH=100%, TMP=100%, TIB=34.5%. No conversion of the oxygenated components was observed.

The hydrogenation product was then reacted as follows:

The same Ni/SiO$_2$ catalyst (10 cc, 1/16"×3/16" extrudate) was charged to the fixed basket of a CSTR (135 cc). The product obtained from the low temperature hydrogenation above was used as the feed. Using reaction conditions of 150 cc/h feed flowrate, 32 SLH H$_2$ flowrate and a reactor pressure of 400 psig, the following results were obtained:

| Temperature (° C.) | 200 | 250 | 275 | 290 |
|---|---|---|---|---|
| SBTBE conversion (%) | 71.5 | 79.9 | 94.1 | 100 |
| DSBE conversion (%) | 0.9 | 34.8 | 91.4 | 100 |
| TMP-2OL conversion (%) | 85.7 | 90.9 | 96.4 | 100 |
| DIB conversion (%) | >90 | >90 | >90 | >90 |
| TIB conversion (%) | 82.8 | 88.9 | 92.3 | 93.3 |
| Alkane Cracking* | 0.03 | 0.06 | 0.33 | 2.83 |

*Refers to product loss via isooctane conversion to dimethylpentane (C7) plus methane.

When hydrogen flow was discontinued there was no noticeable change in the oxygenated materials conversion.

By way of contrast, where no catalyst was employed in step 2, no conversion of oxygenated materials was obtained.

In this two step procedure, diisobutylene is first converted to isooctane; temperatures of about 50–200° C. and elevated pressures are employed. Hydrogen is provided for the conversion. In the second step, somewhat more severe conditions are employed, ie. higher temperatures of about 150° C. to 300° C. and elevated pressure. In this second step hydrogen can be used but is not essential.

EXAMPLE 3

One Step Diisobutylene to Isooctane Process

Using the same feed as in Example 2, the feed is reacted as follows:

A commercial Ni/SiO2 catalyst as used above (30 cc, 1/16"×3/16" extrudate) was charged to an upflow plug flow reactor (0.81" ID, 0.25" OD thermowell). The olefin feed comprised of 55.3% isooctane, 39.1% 2,4,4-trimethylpentene (DIB), 0.9% dimethylhexenes (DMH), 1.0% other trimethylpentenes (TMP), 2.9% trimers, 0.53% sec-butyl-tert-butyl-ether (SBTBE), 0.14% di-sec-butylether (DSBE) and 0.11% 2,4,4-trimethylpentane-2-ol (TMP-2OL) was fed over the catalyst at 150 cc/h, recycle ratio =1, pressure=1,400 psig, average bed temperature of 250° C. and a H2 feed rate of 66 SLH. Under these test conditions, the following conversions were obtained:

| DIB | >99.9% |
|---|---|
| TIB | >99.9% |
| SBTBE | >99.9% |
| DSBE | 88.0% |
| TMP-2OL | >99.9% |
| Alkane Cracking | 0.4% |

Thus, more than 90% of the total oxygenates were removed under the reaction conditions with minimal loss of isooctane due to cracking.

EXAMPLE 4

One Step Diisobutylene to Isooctane Process

The commercial Ni/SIO2 catalyst used above (10 cc 1/16"×3/16" extrudate) was charged to the fixed basket of a CSTR (135 cc). A mixture comprised by weight of 49.2% % isooctane, 49.4% % 2,4, 4-trimethylpentene (DIB), 1.3% trimers (TIB) and 0.11% sec-butyl-tert-butyl-ether (SBTBE) was used as the feed. Reaction conditions were 150 cc/h feed flowrate, 32 SLH H2 flowrate, 250° C., and a reactor pressure of 400 psig. The following conversions were obtained:

| DIB | 96.8% |
|---|---|
| TIB | 98.6% |
| SBTBE | 97.4% |
| Alkane Cracking | 0.3% |

Appropriate conditions for the one step process for converting diisobutylene to isooctane are temperatures generally in the range of 150° C.–300° C. and pressure of 200 psig or higher. Hydrogen is a necessary reactant for conversion of diisobutylene to isooctane.

Where purification of diisobutylene is the desired objective, hydrogen is omitted but otherwise conditions can be much the same.

In carrying out the invention, a number of reaction mechanisms are possible for conversion of the oxygenated impurities including hydrogenation, hydrogenolysis and hydrolysis.

Catalysts which can be used in the conversion of diisobutylene to isooctane and of oxygenates include nickel, molybdemun, platinum, palladium, cobalt, iron, chromium, manganese and copper; mixtures can be used. The catalyst is desirably supported on a conventional support such as silica, alumina and the like, and can comprise 1–80 wt % of the catalyst.

In the two step procedure, diisobutylene containing the oxygenates is first reacted at about 150° C. to 300° C. and elevated pressure in absence of hydrogen to convert the oxygenates to hydrocarbon and water followed by hydrogenation of the diisobutylene to isooctane.

We claim:

1. A process for the removal of close boiling oxygenated impurities from a feed of isooctane and/or diisobutylene containing minor amounts of oxygenated impurities, wherein the impure feed is reacted at conditions of elevated temperature sufficient to convert the oxygenated impurities to reaction products which are readily separable by distillation from diisobutylene or isooctane, and separating diisobutylene or isooctane from the reaction products.

2. The process of claim 1 wherein a hydrogenation catalyst is employed and the conditions involved temperatures in the range to 50 to about 400° C.

3. A two step process for the production of high purity isooctane from a feed of diisobutylene containing 0.1 to about 5.0 wt % of oxygenated impurities which comprises hydrogenating the diisobutylene to isooctane at 50–200° C. and thereafter converting the oxygenated impurities to hydrocarbon and water at 150–300° C.

4. A process for the production of high purity isooctane from a feed of diisobutylene containing 0.1 to about 5.0 wt % of oxygenated impurities which comprises hydrogenating the feed at about 150–300° C.

* * * * *